United States Patent [19]
Buchert

[11] Patent Number: 5,666,956
[45] Date of Patent: Sep. 16, 1997

[54] INSTRUMENT AND METHOD FOR NON-INVASIVE MONITORING OF HUMAN TISSUE ANALYTE BY MEASURING THE BODY'S INFRARED RADIATION

[76] Inventor: Janusz Michal Buchert, 180 Cabrini Blvd., #79, New York, N.Y. 10033

[21] Appl. No.: 650,832

[22] Filed: May 20, 1996

[51] Int. Cl.$^6$ .................................................. A61B 6/00
[52] U.S. Cl. ................................. 128/664; 128/633
[58] Field of Search .......................... 128/633, 664–7; 356/39–41

[56] References Cited

U.S. PATENT DOCUMENTS

| | | | |
|---|---|---|---|
| 3,958,560 | 5/1976 | March | 128/2 A |
| 3,963,019 | 6/1976 | Quandt | 128/2 T |
| 4,014,321 | 3/1977 | March | 128/2 A |
| 4,224,520 | 9/1980 | Greene et al. | 250/338 |
| 4,659,234 | 4/1987 | Brouwer et al. | 374/121 |
| 4,790,324 | 12/1988 | O'Hara et al. | 128/664 |
| 4,797,840 | 1/1989 | Fraden | 364/557 |
| 4,875,486 | 10/1989 | Rapoport et al. | 128/653 |
| 4,882,492 | 11/1989 | Schlager | 250/346 |
| 4,883,953 | 11/1989 | Koashi et al. | 250/226 |
| 4,932,789 | 6/1990 | Egawa et al. | 374/126 |
| 5,009,230 | 4/1991 | Hutchinson | 128/633 |
| 5,024,533 | 6/1991 | Egawa et al. | 374/126 |
| 5,028,787 | 7/1991 | Rosenthal et al. | 250/341 |
| 5,041,723 | 8/1991 | Ishida et al. | 250/339 |
| 5,054,487 | 10/1991 | Clarke | 128/633 |
| 5,068,536 | 11/1991 | Rosenthal | 250/341 |
| 5,070,874 | 12/1991 | Barnes et al. | 128/633 |
| 5,072,732 | 12/1991 | Rapoport et al. | 128/653 |
| 5,086,229 | 2/1992 | Rosenthal et al. | 250/341 |
| 5,119,819 | 6/1992 | Thomas et al. | 128/660 |
| 5,127,742 | 7/1992 | Fraden | 374/129 |
| 5,139,023 | 8/1992 | Stanley et al. | 128/637 |
| 5,140,985 | 8/1992 | Schroeder et al. | 128/632 |
| 5,145,257 | 9/1992 | Bryant et al. | 374/131 |
| 5,146,091 | 9/1992 | Knudson | 250/664 |
| 5,159,936 | 11/1992 | Yelderman et al. | 128/736 |
| 5,167,235 | 12/1992 | Seacord et al. | 128/664 |
| 5,169,234 | 12/1992 | Bohm | 374/128 |
| 5,169,235 | 12/1992 | Tominaga et al. | 374/129 |
| 5,178,464 | 1/1993 | Fraden | 374/129 |
| 5,179,951 | 1/1993 | Knudson | 128/633 |
| 5,267,151 | 11/1993 | Ham et al. | 364/413.09 |
| 5,267,152 | 11/1993 | Yang et al. | 364/413.09 |
| 5,300,778 | 4/1994 | Norkus et al. | 250/339.1 |
| 5,313,941 | 5/1994 | Braig et al. | 128/633 |
| 5,341,805 | 8/1994 | Strovridi et al. | 128/633 |
| 5,360,004 | 11/1994 | Purdy et al. | 128/633 |
| 5,368,038 | 11/1994 | Fraden | 128/664 |
| 5,370,114 | 12/1994 | Wong et al. | 128/633 |
| 5,379,764 | 1/1995 | Barnes et al. | 128/633 |
| 5,381,796 | 1/1995 | Pompei | 128/664 |
| 5,383,452 | 1/1995 | Buchert | 128/633 |

(List continued on next page.)

OTHER PUBLICATIONS

McGraw Hill Encyclopedia of Physics, Second Ed. ISBN 0-07051400-3, 1993, pp. 532–537.
J. S. Maier et al., Optics Letters v19, No. 24 1994 pp. 2062.
M. Kohl et al., Optics Letters, v19, No. 24 1994, pp. 2170.
Hamamatsu Catalog, Oct. 1993 p. 3.
Hamamatsu Catalog, Sep. 93 pp. 26–27.

*Primary Examiner*—Jennifer Bahr
*Assistant Examiner*—Bryan K. Yarnell

[57] ABSTRACT

A method and an instrument for the non-invasive detection of an analyte (e.g. glucose) concentration in human body tissue such as blood is disclosed. The instrument measures analyte (e.g. glucose) concentration by detecting the infrared radiation naturally emitted by a human body using infrared detector with combination of adequate filters such as for example negative correlation filter or narrow band filters or other detector-filter assemblies. The method and instrument is based on the discovery that natural infrared emission from the human body, especially from the tympanic membrane, is modulated by the state of the emitting tissue. Spectral emissivity of human infrared radiation from the tympanic membrane consists of spectral information of the tissue (e.g. blood) analyte (e.g. glucose). This can be directly correlated with the blood analyte concentration, for example, the blood glucose concentration.

9 Claims, 6 Drawing Sheets

U.S. PATENT DOCUMENTS

| | | | |
|---|---|---|---|
| 5,398,681 | 3/1995 | Kupershmidt | 128/633 |
| 5,424,545 | 6/1995 | Block et al. | 250/343 |
| 5,435,309 | 7/1995 | Thomas et al. | 128/633 |
| 5,436,455 | 7/1995 | Rosenthal et al. | 250/339.12 |
| 5,448,992 | 9/1995 | Kupershmidt | 128/633 |
| 5,452,716 | 9/1995 | Clift | 128/633 |
| 5,459,317 | 10/1995 | Small et al. | 250/341.1 |
| 5,460,177 | 10/1995 | Purdy et al. | 128/633 |
| 5,487,607 | 1/1996 | Makita | 374/158 |
| 5,515,847 | 5/1996 | Braig et al. | 128/633 |

INSTRUMENT AND METHOD FOR NON-INVASIVE MONITORING OF HUMAN TISSUE ANALYTE BY MEASURING THE BODY'S INFRARED RADIATION

BACKGROUND OF THE INVENTION

1. Field of the Invention

The present invention relates to a spectroscopic method for measuring the concentration changes of analytes (e.g. glucose) in human body tissues (e.g. blood) using a non-invasive technique which does not require taking a sample from the body for examination. It includes a method and instrument for detecting the infrared radiation naturally emitted by the human body through the use of an infrared detector with a combination of adequate filters such as a negative correlation filter or narrow band filters or other detector-filter assemblies.

The method and instrument is based on the discovery that natural infrared emission from the human body, especially from the tympanic membrane, is modulated by the state of the emitting tissue. Spectral emissivity of human infrared radiation from the tympanic membrane consists of spectral information of the blood analyte. This can be directly correlated with the blood analyte concentration, for example, the glucose concentration.

2. Related Art

The current state of the art in measuring sugar levels in body liquids or foods, fruits and other agricultural products requires taking a sample from the object during the examination process. Special instruments are available for determining blood glucose levels in people with diabetes. The technology uses a small blood sample obtained from a finger prick. The blood is placed on chemically prepared strips and inserted into a portable instrument which analyzes it and provides a blood glucose level measurement. Diabetics must prick their fingers to draw blood for monitoring their glucose levels and some of them must do this many times a day.

To eliminate the pain of drawing blood, as well as to eliminate a source of potential infection, non-invasive optical methods for measuring sugar in blood were invented and use absorption, transmission, reflection or luminescence methods for spectroscopically analyzing blood glucose concentrations.

In U.S. Pat. Nos. 3,958,560 and 4,014,321 to W. F. March, a unique glucose sensor to determine the glucose level in patients is described. The patient's eye is automatically scanned using a dual source of polarized radiation, each transmitting in different wavelengths at one side of the patient's cornea. A sensor located at the other side of the cornea detects the optical rotation of the radiation that passed through the cornea. Because the level of glucose in the bloodstream of the patient is a function (not a simple one) of the glucose level in the cornea, rotation of polarization can determine the level of glucose concentration.

In U.S. Pat. No. 3,963,019 to R. S. Quandt there are described a method and apparatus for detecting changes in body chemistry, for example, in glycinemia, where a beam of light is projected into and through the aqueous humor of the patient's eye. An analyzer positioned to detect the beam on its exit from the patient's eye compares the effect the aqueous humor has on said beam against a norm. The change in the glucose concentration is indicated and detected.

In U.S. Pat. No. 4,882,492 to K. J. Schlager there is described a non-invasive apparatus and related method for measuring the concentration of glucose or other blood analytes. It utilizes both diffuse reflected and transmissive infrared absorption measurements. The apparatus and method utilize non-dispersive correlation spectrometry. Distinguishing the light intensity between the two lights paths, one with a negative correlation filter and the other without one, the apparatus provides a measure proportional to the analyte concentration.

In U.S. Pat. No. 4,883,953 to K. Koashi and H. Yokota there is disclosed a method for measuring the concentration of sugar in liquids by the use of near infrared light. The concentration of sugar in the sample is determined by computing the absorption spectrum of the sugar at various depths in the sample. This is measured by a relatively weak power of infrared light, penetrating close to the surface in a sample, and a relatively strong power of infrared light penetrating relatively deeply in the sample.

In U.S. Pat. No. 5,009,230 to D. P. Hutchinson there is disclosed a device for the non-invasive determination of blood glucose in a patient. This glucose monitor is based on the effect of glucose in a rotating polarized infrared light. More specifically, two orthogonal and equally polarized states of infrared light having minimal absorption are passed through a tissue containing blood, and an accurate determination of change in signal intensity is made due to the angle of rotation of these states. This rotation depends upon the glucose level. The method uses transmission of infrared light through the tissue at a minimum level of absorption of the tissue.

In U.S. Pat. Nos. 5,028,787 and 5,068,536 to R. D. Rosenthal et al. there is disclosed a near-infrared quantitative analysis instrument and method of calibration for non-invasive measures of blood glucose by analyzing near-infrared energy following interactance with venous or arterial blood, or transmission through blood contained in a body part.

In U.S. Pat. No. 5,054,487 to R. H. Clarke there is disclosed a method for non-invasive material analysis, in which a material is illuminated at a plurality of discrete wavelengths. Measurements of the intensity of reflected light at such wavelengths are taken, and an analysis of reflection ratios for various wavelengths are correlated with specific material properties such as concentration of analytes.

Another disclosed method for measuring blood sugar (U.S. Pat. Nos. 5,146,091 and 5,179,951 to Mark B. Knudson) involves testing body fluid constituents by measuring light reflected from the tympanic membrane. The testing light and a reference light at a glucose sensitive wavelength of about 500 to about 4000 wave numbers ($cm^{-1}$) are directed toward the tympanic membrane which contains fluid having an unknown concentration of a constituent. A light detector is provided for measuring the intensity of the testing light and the intensity of the reference light, both of which are reflected and spectrally modified by the fluid. A light path distance measurer is provided for measuring the distance of a light path traveled by the testing light and a reference light. A circuit is provided for calculating the level of the constituent in the fluid in response to a reduction in intensity in both the testing light and the reference light and in response to the measured distance.

In U.S. Pat. No. 5,313,941 there is disclosed a noninvasive pulsed infrared spectrophotometer for measuring the concentration of at least one predetermined constituent of a patient's blood. It consists of an infrared source which emits broadband pulses of infrared light including different wavelengths of at least 2.0 micrometer. It consists of an infrared detector which detects light at said wavelengths and has passed through the arterial blood vessel of the patient and has been selectively absorbed by at least one predetermined constituent.

In another disclosed method (U.S. Pat. No. 5,341,805 to M. Stravridi and W. S. Grundfest) a glucose monitor determines the concentration of glucose in a sample by monitoring fluorescent light produced directly by any glucose present in the sample. It illuminates the sample with ultraviolet excitation light which induces glucose to fluoresce. A detector monitors the return light in two wavelength bands. One wavelength band includes a characteristic spectral peak of glucose fluorescence; the other wavelength band is a reference band having known spectral characteristics. A processor is used to determine the concentration of glucose in the sample.

In U.S. Pat. Nos. 5,360,004 and 5,379,764 to D. Purdy et al. there is disclosed a method and apparatus for noninvasive determination of the concentration of at least one analyte in a mammal. A portion of the mammal's body is irradiated with incident near-infrared radiation, where the incident radiation includes two or more distinct bands of continuous-wavelength incident radiation. The resulting radiation emitted from that portion of the body is sensed and a value for the concentration of the analyte is derived.

In U.S. Pat. No. 5,370,114 to J. Y. Wong et al. there is disclosed a noninvasive blood chemistry measurement apparatus for measuring the concentration of selected blood components. This apparatus is comprised of: a source of exposing light in an infrared spectral region and the means for detecting light emitted from molecules in response to exposing light from said source of light. At least two additional detected signals are monitored and processed at wavenumbers suitable for eliminating temperature and pressure effects on the calculated blood glucose levels.

In U.S. Pat. No. 5,383,452 to J. Buchert there is disclosed a method, apparatus and procedure for the non-invasive detection of sugar concentration changes in blood. The instrument measures sugar concentration changes using natural fingerprints of sugar, a rotation of polarization of light emitted from the biological particle chromophores dissolved with sugar in human liquids. The degree of polarization of light emitted from luminescence centers undergoing interaction with an optically active medium such as sugar is proportional to the concentration of sugar in blood.

In other research (by J. S. Maier et al published in Optics Letters, V. 19, No. 24, Dec. 15, 1994, p.2062 and by M. Kohl et al published in Optics Letters, V. 19, No. 24, Dec. 15, 1994, p.2170) it is shown that the difference in the refractive index between the extracellular fluid and the cellular components can be modulated by tissue glucose levels which affect the refractive index of the extracellular fluid. Researchers designed and constructed a frequency-domain near-infrared tissue spectrometer capable of measuring the reduced scattering coefficient of tissue with enough precision to detect changes in glucose levels in the physiological and pathological range.

Other patents for non-invasively analyzing glucose levels in blood based on various spectroscopic, electrochemical and acoustic velocity measurement methods are as follows:

In U.S. Pat. Nos. 4,875,486 and 5,072,732 to U. Rapoport et al. there is disclosed a nuclear magnetic resonance apparatus, where predetermined water and glucose peaks are compared with the measured water and glucose peaks for determining the measured concentration.

In U.S. Pat. No. 5,119,819 to G. H. Thomas et al. there is disclosed acoustic velocity measurements for monitoring the effect of glucose concentration upon the density and adiabatic compressibility of serum.

In U.S. Pat. No. 5,139,023 to T. H. Stanley at al. there is disclosed a method for non-invasive blood glucose monitoring by correlating the amount of glucose which permeates an epithelial membrane, such as skin, with a glucose receiving medium over a specified time period. The glucose receiving medium is then removed and analyzed for the presence of glucose using a conventional analytical technique.

In U.S. Pat. No. 5,140,985 to J. M. Schroeder et al. there is disclosed a measuring instrument and indicating device which gives an indication of blood glucose by metering the glucose content in sweat, or other body fluids, using a plurality of oxygen sensors covered by a semi-porous membrane. The device can be directly attached to the arm; the measuring device will react with localized sweating and indicate the wearer's blood glucose level.

The above described state of the art in non-invasive blood glucose measurement devices contains many approaches and indicates the importance of the problem. None of the described devices have yet been marketed. Some inventors claim that instruments being developed give accurate blood glucose level readings and can be used for home testing by diabetics. These instruments have limitations stemming from the use of near infrared light for measurement of absorption, transmission or reflectance; in this region of the spectrum one can observe interference in absorption from other chemical components. Analyses based on only one or two wavelengths can be inaccurate if there is alcohol in the blood or any other substances that absorb at the same frequencies. In addition, these analyses can be thrown off by instrument errors, outlier samples (samples with spectra that differ from the calibration set) physiological differences between people (skin pigmentation, thickness of the finger). Methods of near infrared spectroscopy must be coupled with sophisticated mathematical and statistical techniques to distinguish between non-glucose sources and to extract a faint glucose spectral signature. Another limitation of these types of blood glucose testers is that they have to be custom calibrated for each user. The need for individual calibration results from the different combination of water levels, fat levels and protein levels in various people which cause changes in the absorption of near infrared light. Since the amount of glucose in the body is less than one thousandth that of other chemicals (and all of them possess absorption in the near infrared), variations of these constituents which exist among people may make universal calibration unlikely.

Other, non-invasive but also non-direct methods and instruments attempt to determine blood glucose content by measuring the glucose in sweat, saliva, urine or tears. These measurements, which can be quite reliable from the chemical analysis point of view, do not determine blood glucose levels because of the complicated, and not always well-defined, relation between blood glucose levels and glucose concentration in other body fluids. Other invented methods like acoustic velocity measurements in blood, are not very reliable because of the lack of well established and simple relations with blood glucose levels.

None of the above described methods and devices for the non-invasive measurement of blood glucose, or other biological constituents of the human body, explore the fact that the human body naturally emits very strong electromagnetic signals in the micrometer wavelength. Non-invasive optical methods already invented for sugar determination use absorption, transmission, reflection, luminescence or scattering methods in near-infrared or infrared spectral regions for spectroscopically analyzing blood glucose concentration. As in standard spectroscopical methods one needs a source of electromagnetic radiation in certain wavelengths and a means of detecting the resulting transmitted, absorbed, luminescence radiation after it undergoes interaction with a measured medium, e.g. blood or other tissue, to determine the concentration of biological constituents of the human body using a number of technical approaches.

Infrared sensing devices have been commercially available for measuring the temperature of the objects. Infrared thermometry is used in industry to remotely measure process and machinery temperatures. In medical applications these methods are used to measure patients temperature without physical contact. One can measure a patient's skin temperature or, more reliably, patient temperature by quantifying the infrared emission from the tympanic membrane. The tympanic membrane is known to be in an excellent position to measure body temperature because it shares the blood supply with the hypothalamus, the center of core body temperature regulation. The tympanic thermometer uses the ear. It is inserted into the auditory canal so as to sufficiently enclose the detector apparatus such that multiple reflections of the radiation from the tympanic membrane transform the auditory canal into a "black body" cavity, a cavity with emissivity theoretically equal to one. In such a way the sensor can get a clear view of the tympanic membrane and its blood vessels to determine the amount of infrared radiation emitted by the patient's tympanic membrane.

Plank's law states a relationship between radiant intensity, spectral distribution and temperature of the blackbody. As the temperature rises, radiation energy is increased. Radiation energy varies depending on wavelengths. The peak value of the radiant emittance distribution shifts to the short wavelengths side with an increase in temperature, and radiation occurs over a wide wavelength band. Total energy radiated from the blackbody and measured by a noncontact infrared thermometer is a result of the total energy emitted over all the wavelengths. It is proportional to an integral of Planck's equation with respect to all wavelengths. It is described in physics by the Stefan-Boltzman law.

A number of U.S. patents describe a different idea and design of tympanic, noncontact thermometers. As an example one can reference: U.S. Pat. No. 4,790,324 to G. J. O'Hara; U.S. Pat. Nos. 4,932,789 and 5,024,533 to Shunji Egawa et al.; U.S. Pat. Nos. 4,797,840 and 5,178,464 to J. Fraden; U.S. Pat. No. 5,159,936 to M. Yelderman et al.; U.S. Pat. No. 5,167,235 to A. R. Seacord et al.; and U.S. Pat. No. 5,169,235 to H. Tominaga et al. In these patents various technical approaches are described concerning stabilization and calibration of such noncontact thermometers. Commercially few such thermometers are available. These include: Thermoscan Instant Thermometer Model No. HM-2 for home use by Thermoscan Inc., 6295 Ferris Square, Suite G, San Diego, Calif. 92121-3248 and other instruments such as Thermoscan PRO-1 and PRO-LT for clinical use.

SUMMARY OF THE INVENTION

It is a principal object of the present invention to provide an instrument and method for noninvasive analyte concentration measurements, for example blood glucose, which can analyze the spectrum at the natural emission fingerprints region of the analyte in the infrared spectral region.

It is the further object of the present invention to provide the instrument for noninvasive analyte concentration determination, for example blood glucose. The said instrument externally measures the emission intensity of a spectral band of the analyte, for example glucose, in an infrared spectral region.

It is still the further object of the present invention to provide the noninvasive analyte concentration determination by the detection method of naturally emitted electromagnetic radiation from the human body using electronic detection techniques which are sensitive at infrared regions of the spectrum.

It is yet still the further object of this invention to provide a technique for detecting the presence of analyte molecules in the human body by means of measurements of the intensity of the analyte characteristic bands in the infrared spectral region utilizing a non-dispersive correlation spectroscopy method.

It is another object of this invention to provide instruments and methods to measure electromagnetic radiation emitted from the human body which has been spectrally modified by the presence of blood analyte (e.g. glucose) or other tissue analytes but not limited to it, utilizing a negative correlation filter for the detection of said radiation in the infrared spectral region.

It is still another object of this invention to provide instruments and methods to measure electromagnetic radiations emitted from the human body which is spectrally modified by the presence of blood analytes (e.g. glucose) or other tissue analytes but not limited to it, utilizing narrow band and/or neutral density filters for detection of said radiation in the infrared spectral region.

It is yet still another object of this invention to correlate the state of measured emission spectral characteristic with blood analyte (e.g. glucose) or other tissue analyte concentrations.

The present inventions are built on the fact that the human body naturally emits strong electromagnetic radiation in the micrometer wavelengths and is based on the discovery that said radiation consists of the spectral information of the blood analyte (e.g. glucose) or other tissue analyte and can be directly correlated with blood analyte (e.g. glucose) or other tissue analyte concentrations.

The human body emits strong electromagnetic radiation based on the law of physics which states that all objects emit infrared radiation, and the infrared radiation amounts and spectral characteristics of the object are determined by their absolute temperatures as well as by the properties and states of the object.

Planck's law states a relationship between the radiant intensity, spectral distribution, and temperature of the blackbody as follows:

$$W_o(\lambda, T) = 2\pi c^2 h/\lambda^5 (e^{hc/k\pi T} - 1)^{-1}$$

where:

$W_o(\lambda, T)$—spectral radiant emittance [W/cm$^2$ μm],
T—absolute temperature of blackbody [K],
λ—wavelength of radiation [μm],
C—velocity of light=2.998×10$^{10}$ [cm/sec],
h—Plank's constant=6.625×10$^{-34}$ [W sec$^2$],
k—Boltzman constant=1.380×10$^{-23}$ [W sec/K].

Figure 1:
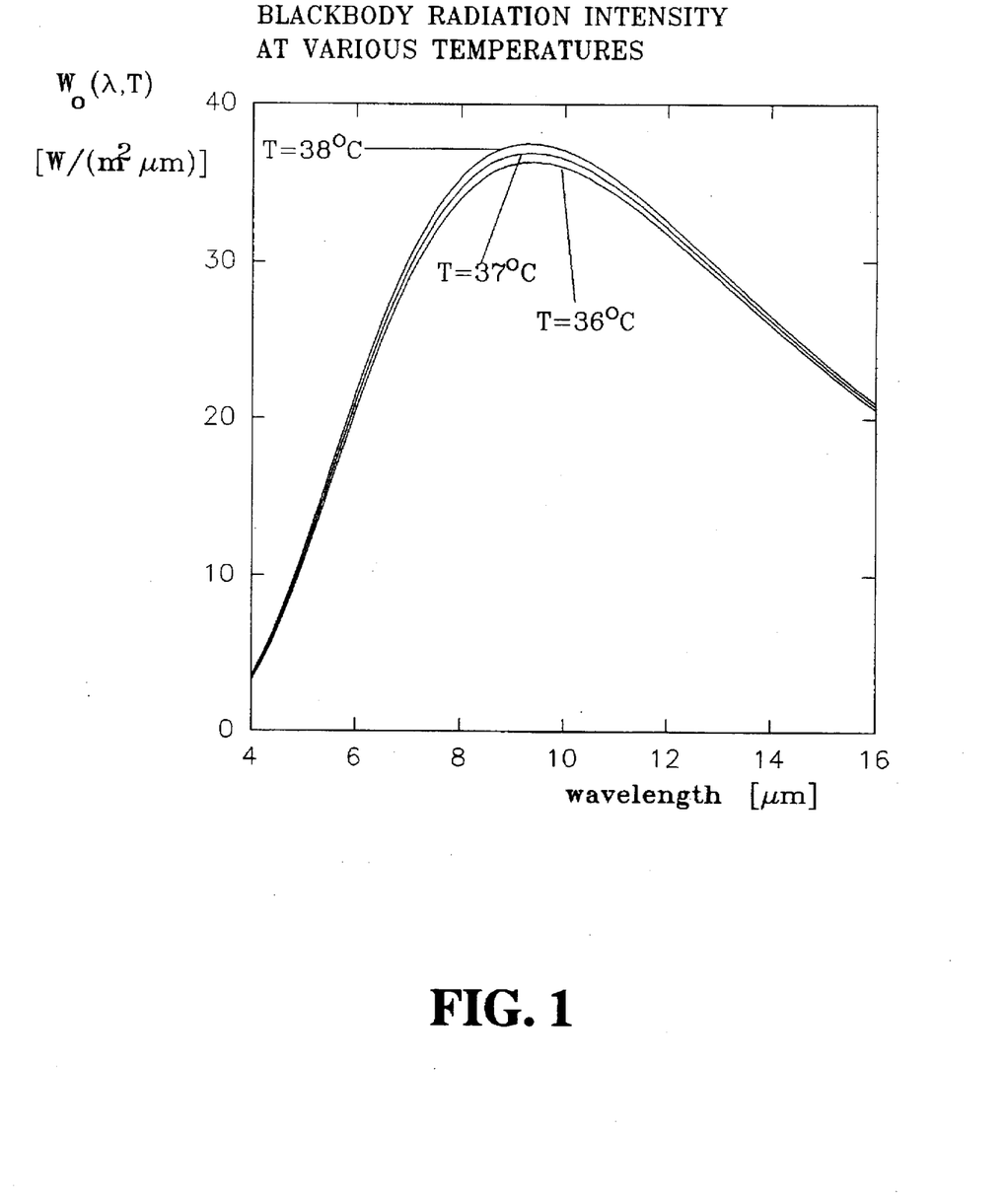
FIG. 1 is a graph showing spectral changes in intensity and in the infrared wavelength spectrum depending on the temperature of the blackbody object.

As the temperature rises, the radiation energy is increased as is shown on FIG. 1. The radiation energy varies depending on wavelengths. The peak value of the radiant emittance distribution shifts to the short wavelengths side with an increase in temperature, and radiation occurs over a wide wavelength band.

The ratio of spectral radiant emittance $W(\lambda,T)$ at a particular wavelength of the non-blackbody radiation to spectral radiant emittance $W_0(\lambda,T)$ of the blackbody at the same wavelength and temperature is called monochromatic emissivity $\epsilon_\lambda$:

$$\epsilon_\lambda = \frac{W(\lambda,T)}{W_0(\lambda,T)}.$$

If the $\epsilon_\lambda$ is constant for all wavelengths, then this kind of body can be called a gray body. Usually in nature we have many materials whose properties are close to the properties of a gray body. For example, human skin tissue has an integral emissivity equal to about 0.986. For the tympanic membrane, which is very well supplied by blood and has very thin skin tissue penetrable by infrared radiation, the monochromatic emmissitivity will be modulated by the spectral characteristic of blood tissue and blood composition will influence it. Kirchhoff's law confirms that for the entire body in the same temperature and for the same wavelength absorptivity $A_\lambda$ is equal to monochromatic emissivity $\epsilon_\lambda$. Thus one can conclude that blood spectral characteristics with different contents of glucose (or other analytes) shown on FIG. 2 will change the emissivity of the tympanic membrane and make it possible to measure the concentration of an analyte (e.g. glucose) in blood.

Radiation from the human body possesses information about spectral characteristics of the object and is determined by absolute body temperatures as well as by the properties and states of the emitting body tissue.

One can measure radiation from the skin of the human body or, more reliably, quantify the infrared emission from the tympanic membrane. The tympanic membrane is known to be in an excellent position to measure, for example, body temperature because it shares the blood supply with the hypothalamus, the center of core body temperature regulation. The tympanic thermometer measures the integral intensity of infrared radiation and uses the ear. It is inserted into the auditory canal so as to sufficiently enclose the detector apparatus such that multiple reflections of radiation from the tympanic membrane transform the auditory canal into a "black body" cavity, a cavity with emissivity theoretically equal to one. In such a way a sensor can get a clear view of the tympanic membrane and its blood vessels for measuring the amount of infrared radiation emitted by the patient's tympanic membrane. This infrared radiation is spectrally modified by the tissue when compared with the theoretical blackbody radiation as shown above in Planck and Kirchhoffs law. Thus infrared radiation has the spectral characteristics of, for example, the blood in the tympanic membrane. This allows measurements of the concentration of blood constituencies by spectral analysis of infrared radiation naturally emitted from the human body.

Spectral characteristics included in electromagnetic radiation from the human body involve information on all components of the tissue. In the invented instrument, spectral characteristic of various constituencies of the tissue will be separated using non-dispersive correlation spectroscopy methods. It relies on the use of a negative correlation filter placed in front of an infrared detector. The negative correlation filter blocks radiation in the absorption bands for the analyte to be measured at one of the infrared detector windows when the other infrared detector window is covered by another filter capable of blocking radiation in such a way that does not include absorption bands characteristic for the analyte at all wavelengths in the range of interest. Distinguishing the radiation intensity between two detector windows, which is done on the detector level because of the physical construction of the detector, provides a measure proportional to analyte concentration and can show for example, the concentration of glucose in blood tissue.

BRIEF DESCRIPTION OF THE DRAWINGS

FIGS. 2a–2d are infrared absorption spectrum:

FIG. 2a of D-glucose;

FIG. 2b of dried human blood with a high level of glucose content;

FIG. 2c of dried human blood with a low level of glucose content;

FIGS. 4a–4c are d diagram of the detector system for infrared radiation of the embodiment of the invention where:

FIGS. 5a and 5b are a plot of measurements of glucose concentration in the blood of a human subject during a glucose tolerance test where:

FIGS. 6a and 6b are a plot of measurements of glucose concentration in the blood of a human subject during a glucose tolerance test where:

DESCRIPTION OF THE PREFERRED EMBODIMENT

The present invention is directed at a an instrument and method for the noninvasive detection of the concentration of analytes in human body tissues, for example, glucose in blood, using naturally occurring infrared radiation in the micrometer spectral region of the human body.

The invented instrument will measure infrared radiation emitted naturally by the human body. This infrared radiation contains spectral information of the emitting body tissue. The radiation thermometer measures the integral energy of infrared radiation from the body through the entire infrared wavelengths without spectral discrimination. In the case of the invented instrument the signal from the detector is proportional to the difference between the intensity of the spectrum emitted from the body passing through the filter with the spectral characteristic of the measured analyte, for example, glucose in blood, and the intensity of the infrared spectrum emitted from the body passing through the filter with spectral characteristics which do not include spectral bands of the analyte. In this way the measured signal is independent from the overall temperature of the emitting body because this information is canceled out by subtraction.

In FIG. 1 is a graph showing the spectral characteristics of blackbody radiation for different temperatures in the infrared spectral region of interest.

Figure 2A:
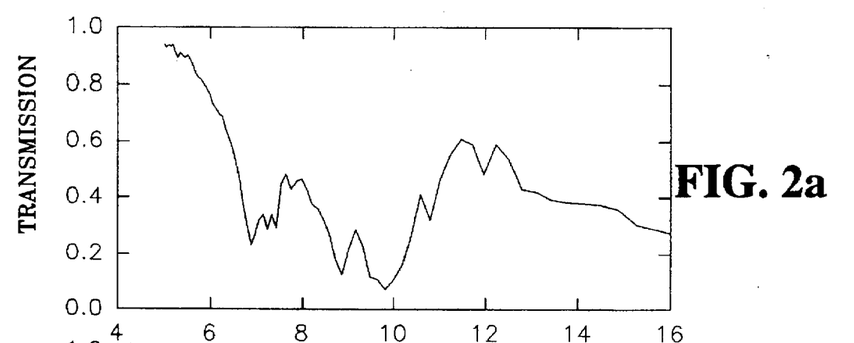

In FIG. 2a is shown the infrared absorption spectrum of D-glucose. The spectrum shows all characteristic bands of interest for glucose in this infrared region. Setting this kind of filter in one of the windows of the infrared detector system and using an appropriate attenuation filter to compensate for the difference in integral intensity absorbed by the first filter, the instrument will measure the concentration of glucose in the human body emitting natural electromagnetic radiation in the infrared spectral region.

Figure 2B:
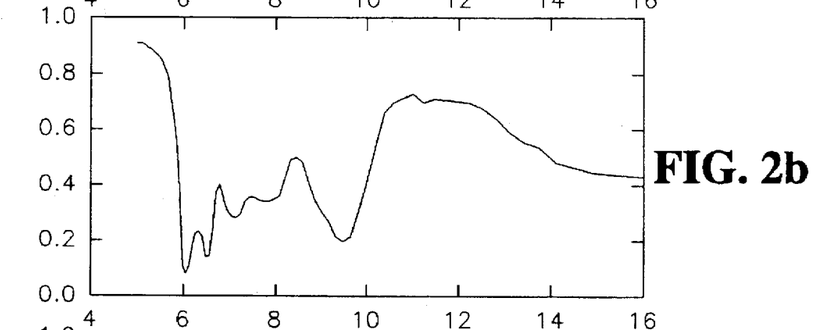
Figure 2C:
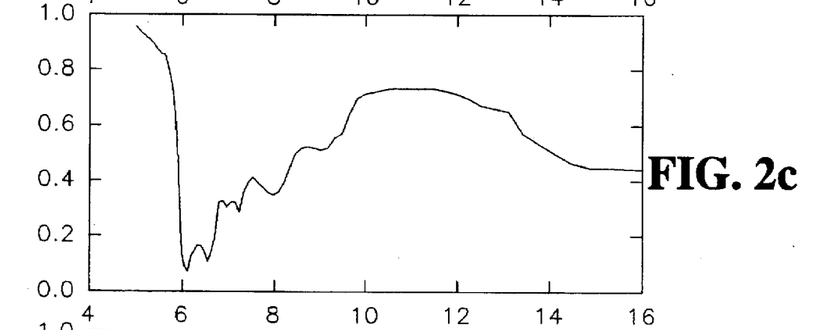
Figure 2D:
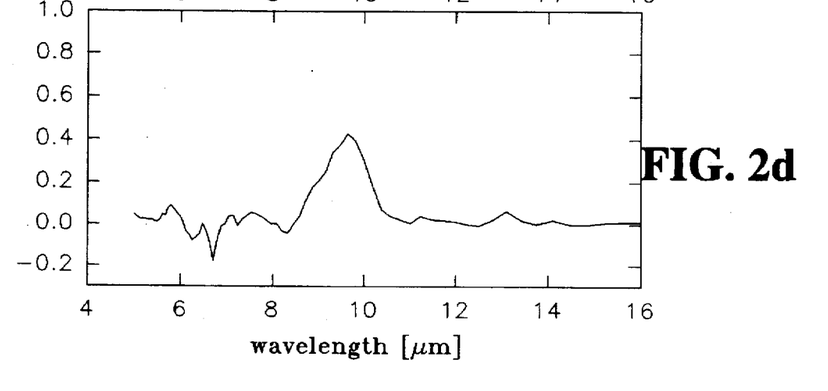
FIG. 2d of the differential spectrum between a high and low level of glucose content in dried human blood which shows one of the spectral characteristics of the invented detector system.

In FIG. 2b is shown an infrared spectrum of dried blood with a high level of glucose content and, in FIG. 2c, one with a low level of blood glucose. A difference spectrum of curve b and curve c is shown in FIG. 2d. The curve in FIG. 2d is the difference spectrum between a high and low content of glucose in dried blood. These spectral absorption characteristics will influence the emissivity of human radiation. This curve also shows the preferred spectral characteristic of the negative correlation filter. An instrument with this kind of filter will have a superior sensitivity and dynamic range for blood glucose measurements. The signal will be directly proportional to the concentration of glucose in blood.

Figure 3:
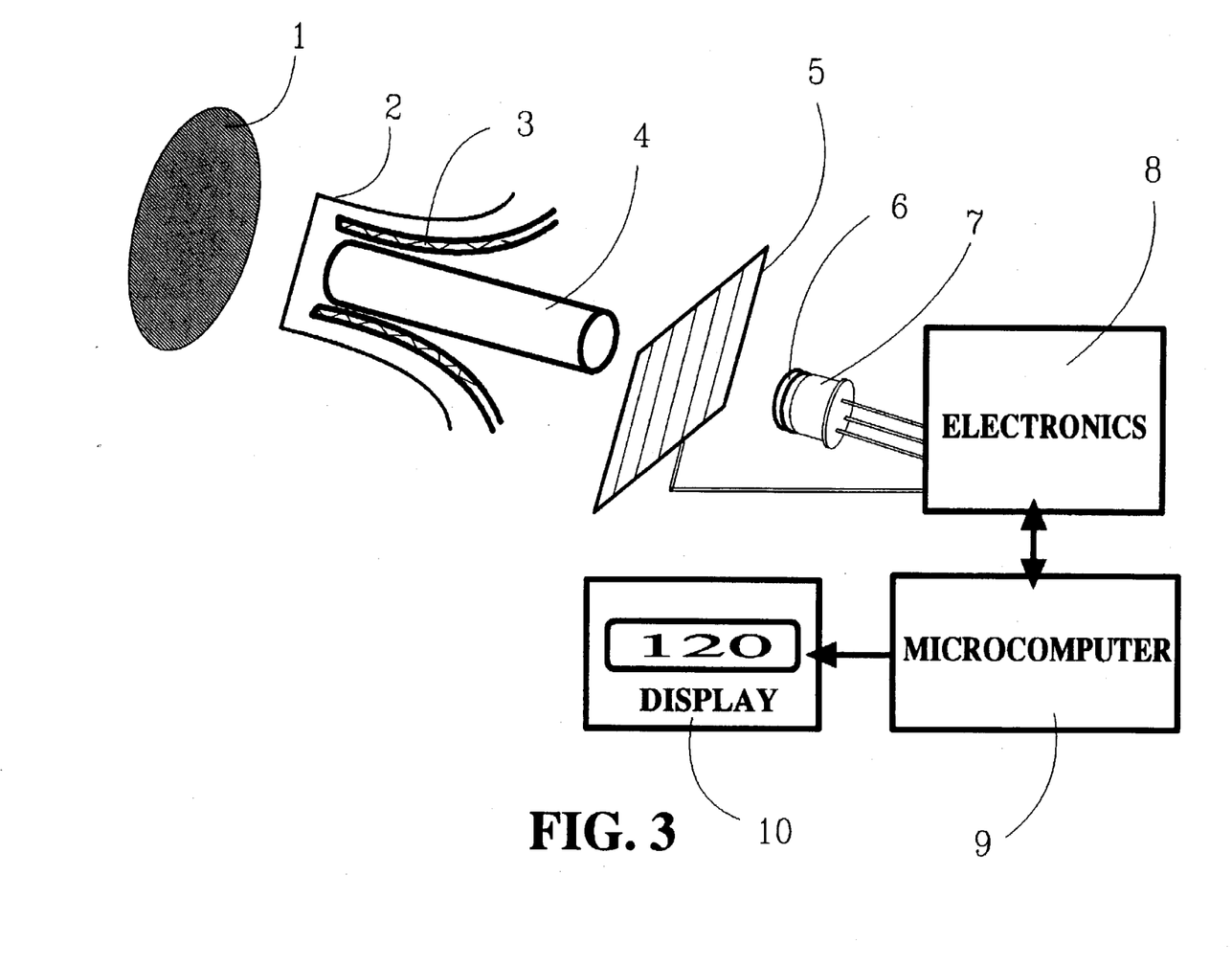
FIG. 3 is a simplified diagram of an embodiment of an instrument of the invention.

In FIG. 3 is shown a simplified diagram of an embodiment of the invented instrument. Infrared radiation from the object target 1 such as a human body is optically received by our instrument. The instrument consists of: the speculum 3 (for insertion, for example, into an ear canal) with a plastic cover 2 (for hygienic reasons, fabricated of a thin polymer material that is transparent to radiation in the far infrared spectral region); the infrared optical system which can include: the infrared wave guide 4 such as a hollow tube polished and/or gold plated inside or a fiber optic transmitting infrared radiation made, for example, from ATRIR special glass produced by Amorphous Materials, Inc.; the optical valve 5; and the detecting system with electronics 8, microcomputer 9 and a display system 10. The said infrared wave guide 4 can be in the form of any directing device such as a mirror, reflector, lens, etc. On the end of the receiving wave guide 4 optical valve 5 is positioned in the form of a shutter or chopper which activates measurements of infrared radiation by a detecting system. The detecting system consists of an optical infrared filter set 6 and a detector 7 sensitive in the infrared region of human body radiation. This infrared sensor (detector 7) can be of any type known to the art. This sensor generates an electrical signal which is representative of the received radiation. The electronic 8, microprocessor 9 and the display system 10 have to stabilize the temperature dependent parts of the instrument, compensate for the ambivient temperature changes, correlate, calculate and then display the concentration of the analyte from the spectral intensity measurements of the infrared radiation emitted by the body.

Figure 4A:
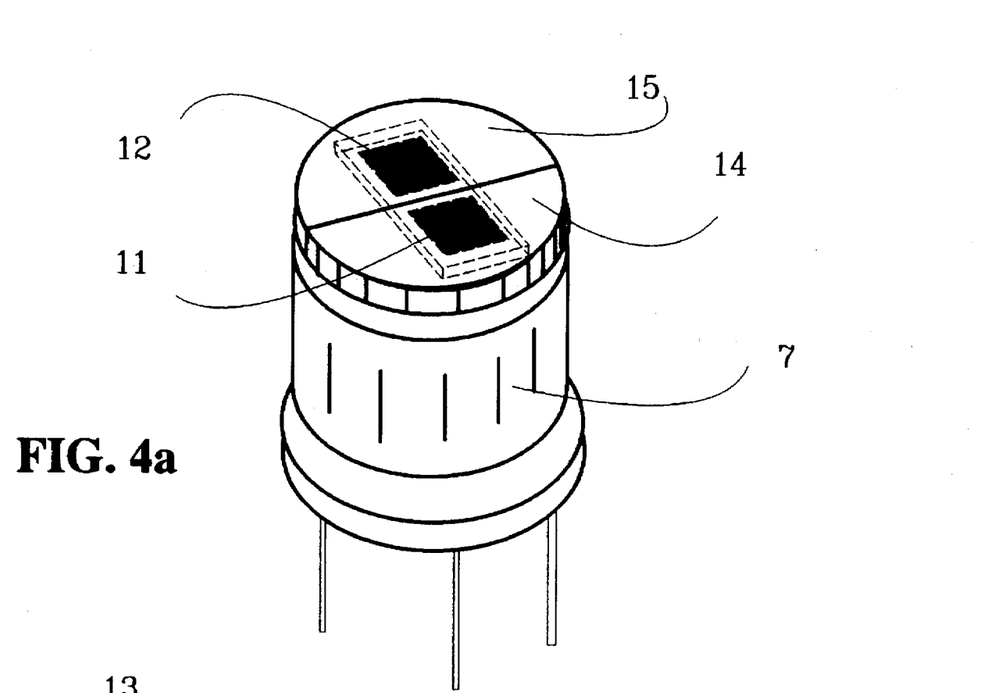
FIG. 4a is a dual-element pyroelectric detector with two different filters covering two sensitive crystal surfaces.
Figure 4B:
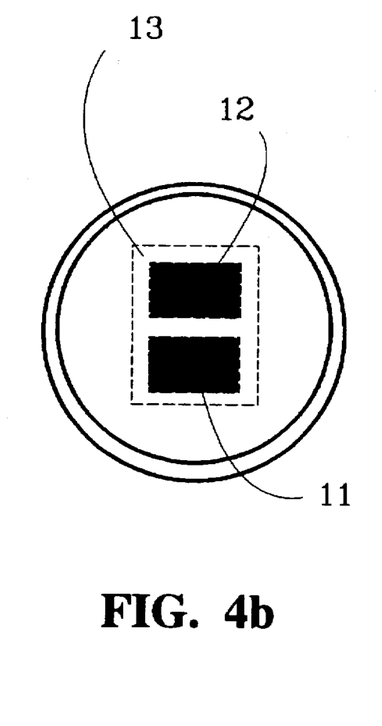
FIG. 4b is a top view of the dual type pyroelectric detector.
Figure 4C:
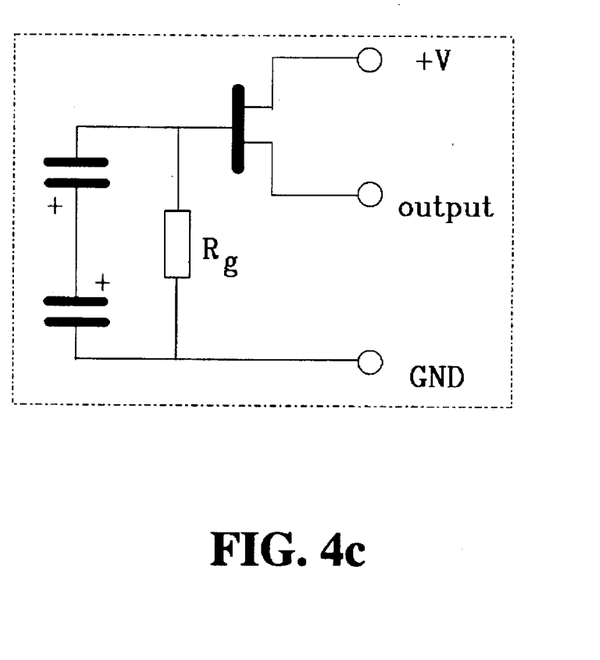
FIG. 4c is a simplified schematic of the sensor circuit.

The detection system which is the main embodiment of the invention consists, for example, of the dual element type P4488 series pyroelectric detector from the Hamamatsu Corporation, Bridgewater, N.J., with two pyroelectric sensing areas 11 and 12 covered by a silicon window 13 with a 5 μm long pass filter (to pass only infrared radiation which corresponds to emission in the range of the internal temperature of a human body) as shown schematically on FIG. 4a. One of the sensing elements 11 is covered by a negative correlation filter when the other sensing area 12 is covered by an appropriate attenuation filter which does not have spectral bands characteristic to the measured analyte. Spectrally modified infrared radiation from, for example, the tympanic membrane illuminates both windows, one with a negative correlating filter which blocks radiation in the absorption bands for the analyte to be measured and the other which passes through a neutral density filter capable of blocking radiation equally at all wavelengths in the range of interest. It is to compensate for overall attenuation by the negative correlating filter in the first sensing area. The two sensing areas 11 and 12 of the detector 7, whose top view is shown on FIG. 4b, are connected so that their outputs are subtracted as shown on the electrical internal detector scheme on FIG. 4c. Difference of the radiation intensity between the two radiation paths provides a measure proportional to the analyte concentration. The electrical signal from the detector is then sent to the forming electronics 8 system and further to the microcomputer 9 and to the display 10 system as shown in FIG. 4. The intensity of this signal is proportional to the spectral difference measured by the detector and thus proportional to the concentration of the body analyte.

One can also use a narrow band filter with the spectral characteristic shown, for example for glucose in blood measurements, in FIG. 2d in front of one of the windows and cover the other by an appropriate attenuation filter or another narrow band filter with a spectral characteristic at a wavelength not sensitive for analyte concentration. Careful adjustment of the peak wavelength and transmission of both narrow band filters can compensate for changes in body temperature. For an attenuation filter with a flat spectral characteristic the signal will be dependent on body temperature because the emission spectrum of body radiation (with the exception of those parts passed by a narrow band filter) will be not canceled out. The method will also have to provide an additional sensor for temperature measurements of the body to compensate for this effect. This method will not be as selective about the analyte to be measured as the above described one with the negative correlation filters based on non-dispersive spectroscopy methods.

As a detector system one can use any, known in the art, wavelength selective system, for example those described in U.S. Pat. No. 4,224,520 by R. F. Green, or in U.S. Pat. No. 5,041,723 by M. Ishida, or in U.S. Pat. No. 5,300,778 by V. Norkus.

Figure 5A:
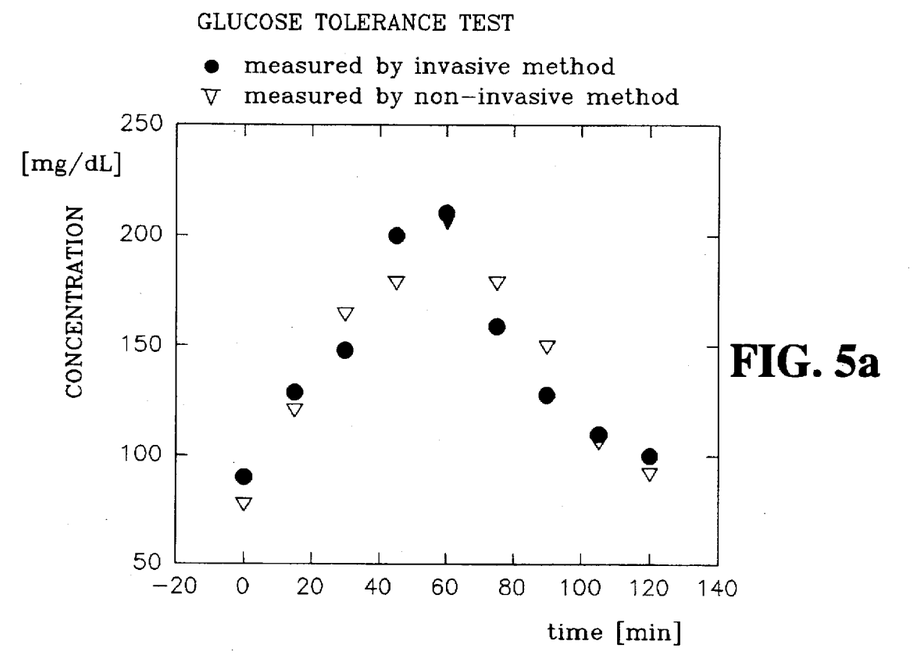
FIG. 5a is a plot of value measured by the invented instrument with a sugar filter and glucose concentration measured using a home blood glucose monitor versus time after the ingestion of table sugar.
Figure 5B:
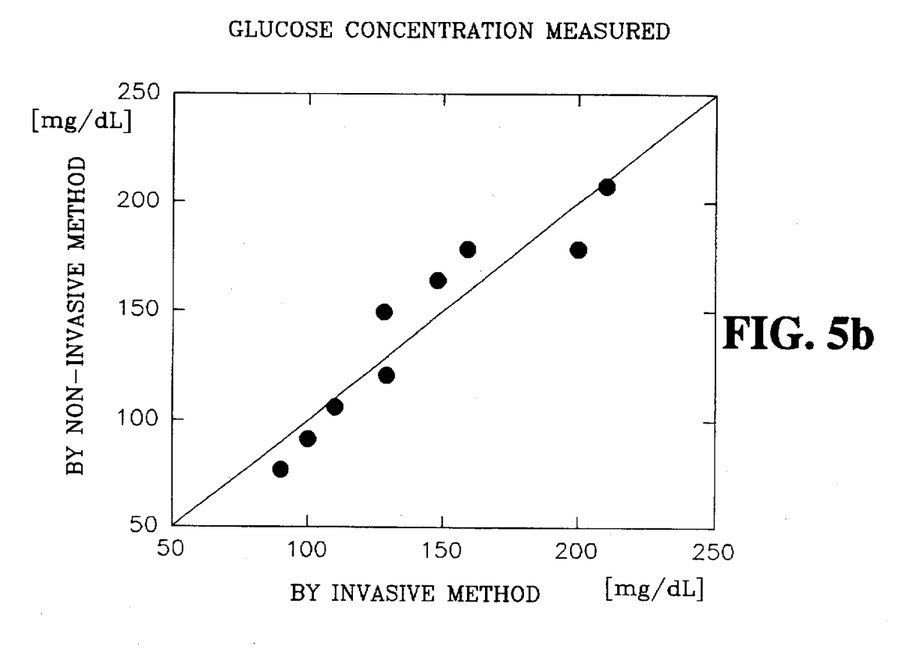
FIG. 5b is a plot of glucose concentration measured using a home blood glucose monitor versus value measured by the invented instrument.
Figure 6A:
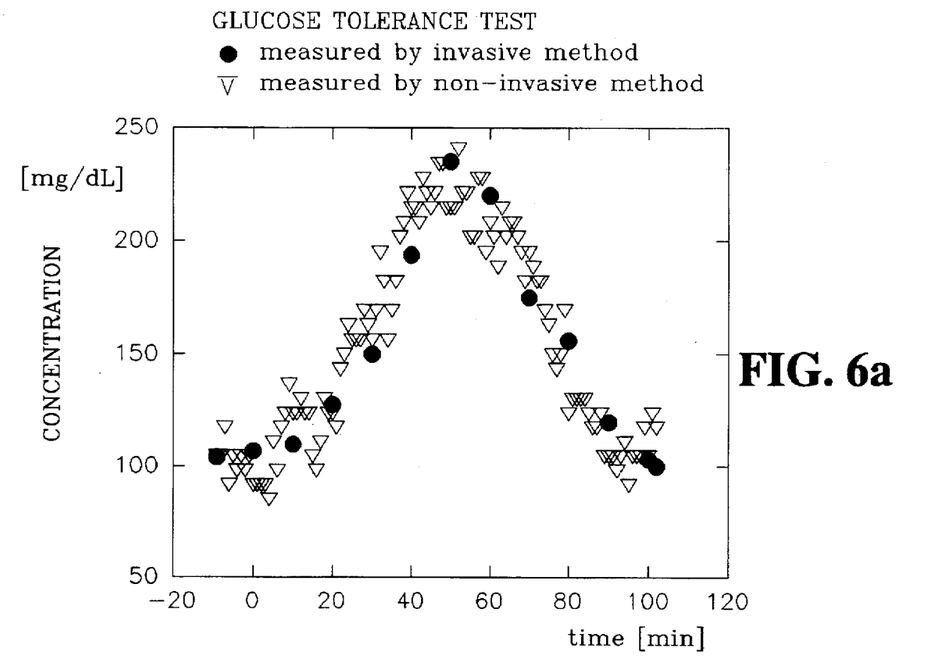
FIG. 6a is a plot of value measured by the invented instrument with a narrow band filter and glucose concentration measured using a home blood glucose monitor versus time after the ingestion of table sugar.
Figure 6B:
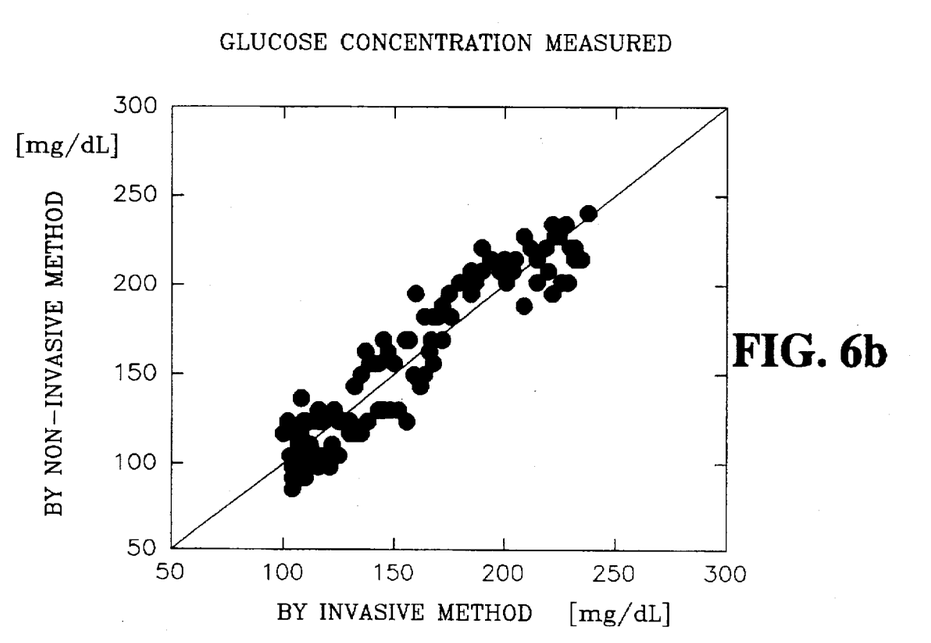
FIG. 6b is a plot of glucose concentration measured using a home blood glucose monitor versus value measured by the invented instrument.

In FIG. 5 and FIG. 6 measurements are shown of the glucose concentration during the glucose tolerance test on a human subject. During the glucose tolerance test the person (non-diabetic) orally ingested about 75 grams of table sugar in a water solution. Glucose concentration in the blood was measured before the experiment and after the ingestion of sugar every 10 or 15 minutes using a home glucose monitor Tracer II made by the Boehringer Mannheim Corporation, Indianopolis, Ind.

During the experiment, with the results shown on FIG. 5, measurements were made using an invented instrument with a sugar filter as a negative correlation filter in one window of the detector and attenuation filters in the other as described previously. A sugar filter was made using a water solution of table sugar covering one of the windows of the detector.

FIG. 5a is a plot of the measurements where hollow triangles show measurements by an invented instrument and black dots show measurements from the home glucose monitor versus the time during which the experiment was performed, where time zero indicates sugar ingestion.

In FIG. 5b a plot of measurements by an invented instrument versus measurements from a home glucose monitor is shown. Points of the measurements from the invented instrument are averages of the three consequent measurements taken in a time difference of not less than 30 seconds. The correlation coefficient for the linear regression is r=0.94.

The filter made of sugar placed on one of the detector windows was not optimized in any way for best performance from the point of view of optimal absorbance. Care was taken only for compensating for the integral intensity entering the other detection window to optimize the resulting electrical signal.

In FIG. 6a is shown a plot of the measurements by an invented instrument with a spectral band filter (hollow triangles, measurements taken every minute); the black dots show measurements from the home glucose monitor (measurements taken every 10 minutes) versus the time during which the experiment was performed, where time zero indicates sugar ingestion.

In FIG. 6b a plot of measurements by an invented instrument versus measurements from a home glucose monitor is shown. The correlation coefficient for the linear regression is r=0.95.

The display unit of the instrument will have a crucial role during the day-to-day operation and will display the concentration of blood glucose for every measurement in diabetic patients. A computer may also store information for keeping records of the measurement of the patient's blood glucose levels.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of determining a human body tissue analyte concentration by non invasive measurement of emission spectral lines characteristic to a body tissue analyte in an infrared spectral region emitted naturally by a human body as heat, comprising:
   a. measuring a spectral intensity of said emission spectral lines;
   b. said emission spectral lines having a wavelength dependence of tissue constituents;
   c. detecting the emission spectral lines at a predetermined emission wavelength;
   d. analyzing the emission spectral lines in said infrared spectral region;
   e. correlating said spectral intensity of emission spectral lines with body analyte concentrations.

2. A method as in claim 1, for determining blood glucose concentration by non-invasive measurement of emission spectral lines characteristic to a body tissue analyte in an infrared spectral region emitted naturally by a human body's tympanic membrane in an infrared wavelength spectrum as heat.

3. An instrument for determining a human body tissue analyte concentration by non-invasive measurement of emission spectral lines characteristic to a body tissue analyte in an infrared spectral region emitted naturally by a human body as heat, comprising:
   a. a means for detecting said emission spectral lines at a predetermined infrared wavelength;
   b. a means for detecting a spectral intensity of the emission spectral lines;
   c. a means for correlating the intensity of emission spectral lines with the tissue analyte concentration.

4. The instrument of claim 3, wherein the detecting means comprises a detector means and an analyzing means for a wavelength selecting means of the emission spectral lines; detector means for detecting the intensity of received emission spectral lines from said analyzing means producing an electronic output signal, and wavelength selecting means for allowing only significant wavelengths of tissue analyte emission spectral lines an natural infrared radiation emitted by the human body to reach the detector means.

5. The instrument of claim 4, wherein the detector means is an infrared energy sensor.

6. The instrument of claim 4, wherein the analyzing means comprises a filter means for filtering the emission spectral lines to allow only wavelengths significant to the tissue analyte emission spectral lines to pass or to be absorbed before reaching the detector means.

7. The instrument of claim 3, where the correlating means is an electronic means comprises electronic amplifiers, signal conditioners and a microcomputer for correlating a state of the electronic output signal from the detecting means with the tissue analyte concentration.

8. An instrument of claim 3 for non-invasive blood glucose concentration measurement based on measurement of emission spectral lines characteristic to a body tissue analyte in an infrared spectral region emitted naturally by a human body tympanic membrane in an infrared wavelength spectrum as heat.

9. An instrument for non-invasive tissue analyte concentration measurement based on measurement of emission spectral lines characteristic to a human body tissue analyte in an infrared spectral region emitted naturally by a tympanic membrane as heat, comprising:
   a. a speculum for insertion into an ear canal;
   b. a plastic cover made of a material transparent to radiation in an infrared spectral region;
   c. an infrared wave guide for receiving infrared radiation from the tympanic membrane and for illuminating all windows of a detecting system;
   d. the infrared wave guide is selected from the group consisting of a mirror, reflector, lens, hollow tube, and a fiber optic;
   e. an optical valve consisting of a shutter or chopper;
   f. the detecting system consisting of an optical infrared filter set and a detector sensitive in an infrared region of human body heat radiation;
   g. an optical infrared filter set consisting of a negative correlating filter or narrow band filters;
   h. a detector system sensitive in the infrared region of human body heat radiation consisting of at least two sensing areas electronically connected so that their outputs are subtracted;
   i. said detector connected with electronics, a microprocessor and a display system for forming, calculating, and displaying an electrical signal from the detector to show a numerical value of the analyte concentration.

* * * * *